US00PP31293P2

(12) United States Plant Patent
Bacon

(10) Patent No.: US PP31,293 P2
(45) Date of Patent: Dec. 31, 2019

(54) GRAPEVINE PLANT NAMED 'SUGRAFIFTYFOUR'

(50) Latin Name: *Vitis vinifera*
Varietal Denomination: Sugrafiftyfour

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 16/350,360

(22) Filed: Nov. 6, 2018

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 6/88
See application file for complete search history.

*Primary Examiner* — Anne Marie Grunberg
(74) *Attorney, Agent, or Firm* — Knobbe, Martens, Olson & Bear, LLP

(57) ABSTRACT

A new and distinct variety of grapevine 'Sugrafiftyfour' is characterized by broad elliptic, very large, very firm berries. The new variety of grapevine has large berry clusters with ripening beginning in early August. The berries of 'Sugrafiftyfour' have nearly no seed trace.

1 Drawing Sheet

Latin name of the genus and species claimed: *Vitis vinifera.*

Variety denomination: 'SUGRAFIFTYFOUR'.

BACKGROUND AND SUMMARY OF THE INVENTION

This application relates to the discovery and asexual propagation of a new and distinct variety of grapevine, 'Sugrafiftyfour', as herein described and illustrated. The new variety was first selected as breeder number 'GR472W' by Terry A. Bacon in Wasco, Kern County, Calif. in 2014. The variety was originated by controlled hybridization.

The new variety 'Sugrafiftyfour' is characterized by broad elliptic, green berries that are very large and very firm. The berries form large clusters and ripen in early August in the area of Wasco, Kern County, Calif. The berries of 'Sugrafiftyfour' have almost no seed trace.

The seed parent is the varietal selection 'Sugrathirtyfive' (U.S. Plant Pat. No. 20,491) and the pollen parent is the varietal selection 'GtR233W' (unpatented breeding selection). The parent varieties were first crossed in April 2011. The date of first sowing was March 2012, and the date of first flowering was April 2014.

The new variety 'Sugrafiftyfour' was first asexually propagated in December 2014 in Wasco, Kern County, Calif., by Terry A. Bacon using hardwood cuttings.

The new variety 'Sugrafiftyfour' resembles its seed parent 'Sugrathirtyfive' in appearance and color, but the fruit of the new variety 'Sugrafiftyfour' begins ripening about August 10th compared to September 1st for 'Sugrathirtyfive'. The new variety also differs from the seed parent in that the flavor of the berries of the new variety is a pronounced combination of muscat and tropical aromas, while the berries of 'Sugrathirtyfive' have a neutral to slightly muscat flavor. The new variety also has a cluster weight of 750 g compared to 800 g for 'Sugrathirtyfive'.

The new variety 'Sugrafiftyfour' differs from its pollen parent 'GR233W' in that the fruit of the new variety begins ripening about August 10th compared to October 13th for 'GR233W'. The new variety 'Sugrafiftyfour' also differs from its pollen parent in that the flavor of the berries of the new variety is a pronounced combination of muscat and tropical aromas while 'GR233W' has a neutral flavor.

The berries of the new variety 'Sugrafiftyfour' have a similar color and shape to the berries of 'Autumn King' (U.S. Plant Pat. No. 16,284) (unpatented). However, the berries of the new variety begin ripening on August 10th compared to September 20th for 'Autumn King'. In addition, the cluster weight of the new variety is about 750 g compared to 700 g for 'Autumn King'. The new variety 'Sugrafiftyfour' also differs from 'Autumn King' in that the flavor of the berries of the new variety is a pronounced combination of muscat and tropical aromas while the berries of 'Autumn King' have a neutral flavor. The berries of the new variety 'Sugrafiftyfour' differ from both 'Autumn King' and 'Thompson Seedless' (unpatented) in that the berries of the new variety have nearly no seed trace compared to rudimentary seeds for the berries of 'Autumn King' and 'Thompson Seedless'. The new variety 'Sugrafiftyfour' also differs from 'Thompson Seedless' in that the berries of the new variety have a broad elliptic berry shape and a cluster weight of 750 g compared to a cylindrical to ovoid berry shape and a cluster weight of 550 g for 'Thompson Seedless'. Additionally, 'Thompson Seedless' begins ripening earlier than "Sugrafiftyfour', on about July 27$^{th}$ compared to August 10$^{th}$ for 'Sugrafiftyfour'.

The new 'Sugrafiftyfour' variety has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration shows typical specimens of the foliage and fruit of the present new grape variety 'Sugrafiftyfour'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to a six year old 'Sugrafiftyfour' plants grown in the vicinity of Wasco, Kern County, Calif. during 2018, and is believed to apply to plants of the variety grown under similar conditions of soil and climate elsewhere.

VINE

General: (Measurements taken on a six year old plant).

- *Vine size*.—Large. Height: Approximately 2.0 m. Width: Approximately 2.5 m.
- *Vigor*.—Vigorous.
- *Density of foliage*.—Dense.
- *Productivity*.—Very productive.
- *Crop load*.—Approximately 27 kg per vine after thinning.
- *Own root*.—Yes.
- *Training method*.—Typically cane pruned leaving six canes.
- *Resistance*.—Average resistance and susceptibility to diseases or pests of *Vitis vinifera* species.

Trunk:

- *Shape*.—Stocky.
- *Diameter*.—Approximately 7.5 cm (at 30 cm above the soil line).
- *Straps*.—Short.
- *Surface texture*.—Medium shaggy.
- *Inner and outer bark color*.—Outer bark about Medium Greyed-Orange 177C and inner bark about Medium Greyed-Red 178D.

SHOOTS

Young shoot:

- *Form of tip*.—Half open.
- *Intensity of anthocyanin coloration of tip*.—Absent or very weak.
- *Density of prostrate hairs on tip*.—Absent or very sparse.
- *Density of erect hairs on tip*.—Absent or very sparse.
- *Color*.—About Medium Yellow-Green 144B.

Woody shoot (observations made in the middle third of shoot):

- *Attitude before tying*.—Semi-drooping.
- *Growth of axillary shoots*.—Medium, mainly 17 cm to 21 cm.
- *Internode length*.—Medium, approximately 120 mm.
- *Width at node*.—Approximately 13 mm.
- *Cross section*.—Circular.
- *Surface texture*.—Striated.
- *Main color*.—About Medium Greyed-Orange 166C.
- *Color of dorsal side of internode*.—About Medium Greyed-Orange 166C.
- *Color of ventral side of internode*.—About Medium Greyed-Orange 166D.
- *Color of dorsal side of node*.—About Medium Yellow-Green 146C with Medium Greyed-Orange 166D.
- *Color of ventral side of node*.—About Medium Yellow-Green 146C with Medium Greyed-Orange 166D.
- *Density of erect hairs on nodes*.—Absent or Very Sparse.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Discontinuous.
- *Thickness*.—Approximately 4 mm.
- *Color*.—About Light Yellow-Green 148D in mid-summer.
- *Form*.—Bifurcated.
- *Number of consecutive tendrils*.—Up to two.
- *Length of tendril*.—Medium, approximately 15 cm.

LEAVES

Young leaves:

- *Color of upper surface of first* 4 *distal unfolded leaves*.—About Medium Yellow-Green 144B.
- *Average intensity of anthocyanin coloration of six distal leaves prior to flowering*.—Absent.
- *Density of prostrate hairs between veins at lower surface of* 4*th distal unfolded leaf*.—Absent or very sparse.
- *Density of erect hairs between veins at lower surface of* 4*th distal unfolded leaf*.—Absent or very sparse.
- *Density of prostrate hairs on veins at lower surface of* 4*th distal unfolded leaf*.—Absent or very sparse.
- *Density of erect hairs on veins at lower surface of* 4*th distal unfolded leaf*.—Absent or very sparse.

Mature leaves (observations made on leaves in the middle third of shoot):

- *Average length*.—Large, approximately 145 mm.
- *Average width*.—Large, approximately 190 mm.
- *Shape of blade*.—Pentagonal.
- *Number of lobes*.—Approximately five.
- *Mature leaf profile*.—Undulate.

*Blistering surface of blade upper surface.*—Absent or very weak.
*Leaf blade tip.*—In the plane of the leaf.
*Undulation of margin.*—Slight.
*Thickness.*—Average — typical of *Vitis vinifera* species.
*Overall shape of teeth.*—Mixture of both sides straight and both sides convex.
*Length of teeth.*—Medium, ranging from about 5 mm to 10 mm.
*Ratio length/width of teeth.*—Very small, nearly 1:1.
*General shape of petiole sinus lobes.*—Half open.
*Tooth at petiole sinus.*—Absent.
*Petiole sinus limited by veins.*—Absent.
*Shape of upper lateral sinus lobes.*—Slightly overlapping.
*Depth of upper lateral sinuses.*—Medium, approximately 20 mm to 40 mm.
*Density of prostrate hairs between veins on lower surface of blade.*—Absent to very sparse.
*Density of erect hairs between veins on lower surface of blade.*—Absent to very sparse.
*Density of prostrate hairs on main veins on lower surface of blade.*—Absent to very sparse.
*Density of erect hairs on main veins on lower surface of blade.*—Absent to very sparse.
*Density of prostrate hairs on main veins on upper surface of blade.*—Absent to very sparse.
*Autumn coloration of leaves.*—Mainly about Dark Green 137A but some leaves are mixed Dark Green 137A with Dark Greyed-Purple 187A and Dark Yellow-Green 154A.

Upper leaf surface:
*Color.*—About Dark Green 137A.
*Surface texture.*—Smooth.
*Surface appearance.*—Dull.
*Anthocyanin coloration of main veins.*—Absent or very sparse.

Lower leaf surface:
*Color.*—About Medium Green 137C.
*Surface texture.*—Smooth.
*Surface appearance.*—Dull.
*Anthocyanin coloration of main veins.*—Absent or very sparse.

Petiole:
*Length of petiole.*—Approximately 60 mm to 80 mm.
*Diameter.*—Approximately 3 mm.
*Length of petiole compared to middle vein.*—Nearly equal.
*Density of prostrate hairs on petiole.*—Absent.
*Density of erect hairs on petiole.*—Absent.
*Color.*—About Medium Green 138B, sometimes with highlights of Medium Red 46C.

Buds:
*Shape.*—Conical.
*Size.*—Medium, approximately 3 mm wide×4 mm long.
*Position.*—Slightly held out.
*Bud fruitfulness.*—Good fertility, mostly fruitful in 3$^{rd}$ to 5$^{th}$ bud position with 1 to 2 clusters per shoot.
*Time of bud burst.*—Late, approximately March 24$^{th}$, for the region of the Southern San Joaquin Valley, Calif.

FLOWERS

General:
*Flower type.*—Fully developed stamen and fully developed gynoecium.
*Position of first flowering node.*—Usually 3$^{rd}$ to 5$^{th}$ node of current season growth.
*Number of inflorescences per shoot.*—Approximately 1 to 2, average 1.5.
*Time of full bloom.*—Late for the area of the Southern San Joaquin Valley, Calif. Approximately May 7$^{th}$.

FRUIT

General:
*Ripening period.*—Midseason, beginning about August 10$^{th}$ with mid-ripe about August 15$^{th}$ in the area of the Southern San Joaquin Valley, Calif.
*Use.*—Fresh market.
*Storage quality.*—Excellent.

Cluster:
*Form.*—Conical, shouldered.
*Cluster size (peduncle excluded).*—Large.
*Cluster length (peduncle excluded).*—Approximately 250 mm.
*Cluster width.*—Approximately 170 mm.
*Cluster weight.*—Approximately 750 g.
*Cluster density.*—Medium, loose and full.
*Number of berries.*—Approximately 70-90.

Peduncle:
*Length.*—Medium, approximately 20 mm.
*Diameter.*—Approximately 6 mm.
*Lignification of peduncle.*—Weak.
*Color.*—About Medium Green 138B.

Berry:
*Size.*—Very large, approximately 10 g.
*Dimensions.*—Longitudinal axis: Approximately 35 mm. Horizontal axis: Approximately 28 mm.
*Uniformity of size.*—Nearly uniform.
*Shape.*—Broad elliptic.
*Cross section.*—Circular.
*Skin color (without bloom).*—About Medium Yellow-Green 144B to Medium Yellow-Green 146C.
*Flesh color.*—About Medium Yellow-Green 144C.
*Anthocyanin color of flesh.*—Absent or very weak.
*Bloom (cuticular wax).*—Medium.
*Pedicel length.*—Approximately 7 mm.
*Pedicel thickness.*—Medium, approximately 1.8 mm.
*Berry separation from pedicel.*—Moderately easy.
*Seed traces.*—Berries contain nearly no seed trace.
*Berry firmness.*—Very firm.
*Flesh juiciness.*—Juicy.
*Flesh texture.*—Crisp.
*Particular flavor.*—Flavor is pronounced combination of muscat and tropical.
*Refractometer test.*—Approximately 19 Brix.
*Juice pH.*—Approximately 3.2.
*Titratable acidity.*—Approximately 0.49%.
*Brix:acid ratio.*—Approximately 38.8.

Skin:
*Skin thickness.*—Medium, about 175 μm.
*Skin texture.*—Smooth.

*Skin reticulation*.—Absent.

*Skin tenacity*.—Tenacious to flesh.

*Skin tendency to crack*.—Low.

*Skin sensitivity to sunburn*.—Low to moderate.

What is claimed is:

1. A new and distinct variety of grapevine as herein illustrated and described.

* * * * *

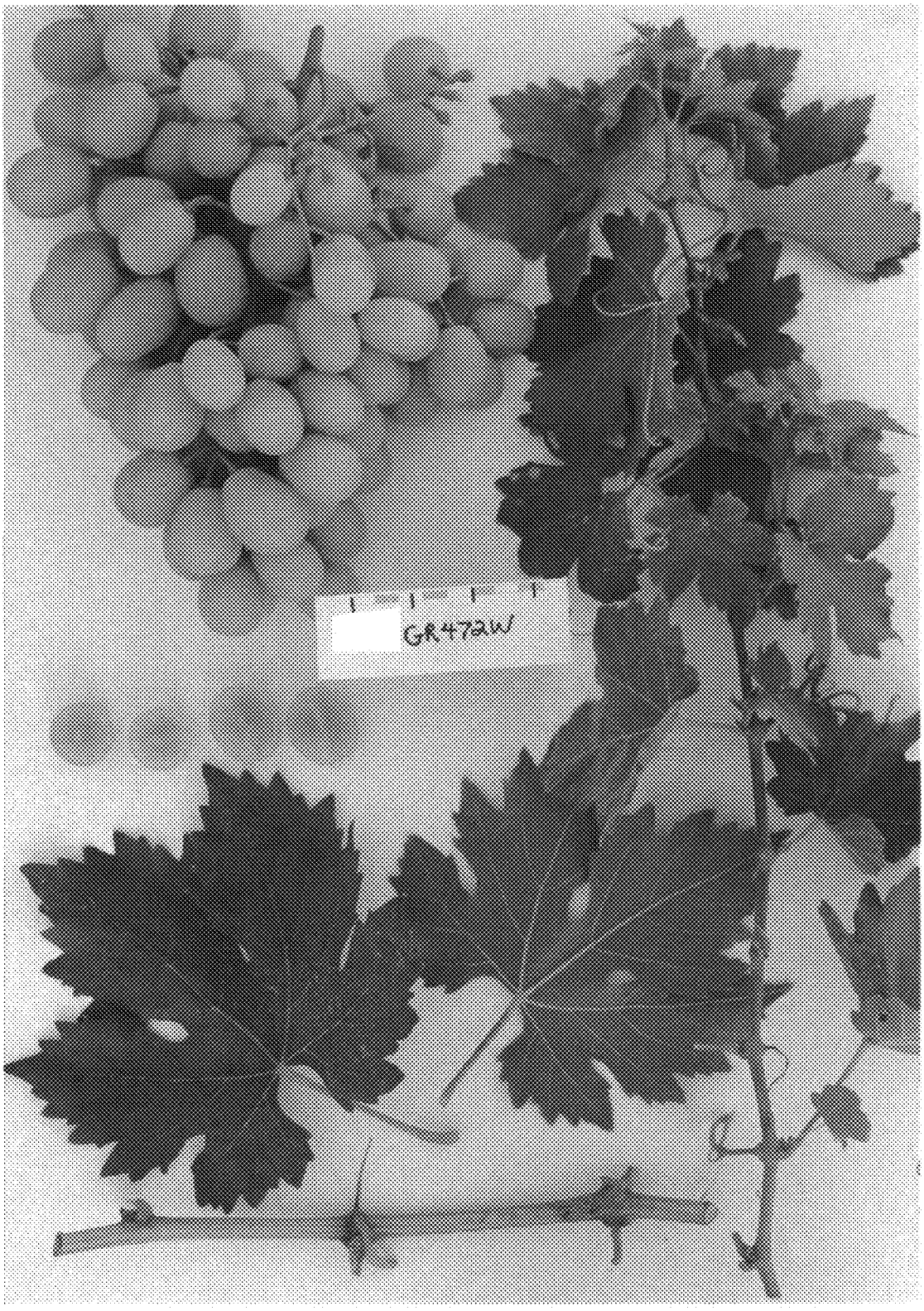
GR472W